United States Patent [19]

Berg

[11] Patent Number: 4,902,618
[45] Date of Patent: Feb. 20, 1990

[54] PRODUCTION OF HYBRIDOMA ANTIBODIES FOR INTERFERON

[75] Inventor: Kurt F. Berg, Gentofte, Denmark

[73] Assignee: Wadley Technologies, Inc., Dallas, Tex.

[21] Appl. No.: 840,136

[22] Filed: Mar. 14, 1986

Related U.S. Application Data

[63] Continuation-in-part of Ser. No. 586,019, Feb. 3, 1984, abandoned.

[30] Foreign Application Priority Data

Feb. 4, 1983 [DK] Denmark ............................. 457/83

[51] Int. Cl.[4] ...................... C12N 15/00; C12N 5/02; C12P 21/00; A61K 39/395
[52] U.S. Cl. ........................... 435/172.2; 435/240.27; 435/70.21; 935/93; 935/104; 424/85.8
[58] Field of Search .................. 435/68, 172.2, 240.27, 435/811, 948; 436/548; 935/104, 110, 93; 424/85, 88; 530/387

[56] References Cited

U.S. PATENT DOCUMENTS

4,350,683  9/1982  Galfre et al. ........................... 424/85
4,423,147  12/1983  Secher et al. ........................... 435/68

OTHER PUBLICATIONS

"Identification, Production, and Characterization of Murine Monoclonal Antibody (LO-22) Recognizing 12 Native Species of Human Alpha Interferon", *Journal of Interferon Research,* 4:481–491 (1984), by Berg.

"Purification and Structural Analysis of Interferon", *Phil. Trans. R. Soc.* (London), 299:39–50 (1982) by Rubenstein.

Booklet "Purification and Characterization of Murine and Human Interferons", *Acta Pathologica, Microbiologica et Immunologica Scandinavica,* Section C, Supplement No. 279 (1982), by Berg.

"Monoclonal Antibodies: Production and Maintenance", London, pp. 1–65 (1982), by Lovborg.

"Monoclonal Antibodies to Human Alpha-Interferon and Their Use for Affinity Chromatography", *The Journal of Immunology,* 129:2244–2247 (1982), by Novick et al.

"Demonstration of Two Subtypes of Human Leukocyte Interferon (IFN-Alpha) by Monoclonal Antibodies", *The Journal of Immunology,* 128:2824–2825 (1982), by Imai et al.

"Production of Hybridomas Secreting Monoclonal Antibodies to the Human Leukocyte Interferons", *Proceedings of the National Academy of Sciences* (U.S.A.), 78:1848–1852 (1981), by Staehelin et al.

"Plasmacytomas and Hybridomas—Development and Applications", *Monoclonal Antibodies and Hybridomas: A New Dimension in Biological Analysis,* Editors Kennett, R. H., et al, pp. 3–17 (1980), Plenum Press, New York, NY.

"A Family of Structural Genes for Human Lymphoblastoid (Leukocyte-Type) Interferon", *Nature,* 287:408–411 (1980), by Allen and Fantes.

"The Complete Purification of Human Leucocyte Interferon", *Scand. J. Immunol.,* 11:489–502 (1980), by Berg and Heron.

"Cloning and Partial Nucleotide Sequence of Human Immunoglobulin Chain cDNA from B Cells and Mouse-Human Hybridomas", *Proc. Natl. Acad. Sci.* (U.S.A.), 77:6027–6031 (1980), by Dolby et al.

"Isolation of a Cell Hybrid Which Produces Antibodies Specific for Human Leukocyte Interferon", *C. R. Academy of Sciences* (Paris) 291:893–896 (1980), by Montagnier et al.

"Cloning of Human Immunoglobulin Gene and Comparison with Mouse Gene", *Nucleic Acids Research,* 8–5983–5991 (1980), by Takahashi et al.

"A Monoclonal Antibody for Large-Scale Purification of Human Leukocyte Interferon", *Nature,* 285:446–450 (1980), by Secher and Burke.

"Antigenic Properties of Human Lymphoblastoid Interferons", *Infection and Immunity,* 23:244–248 (1979), by Dalton and Paucker.

"Purification of Human Interferon by Antibody Affinity Chromatography, Using Highly Absorbed Anti-Interferon", *Scand. J. Immunol.,* 8:429–436 (1978), by Berg et al.

"Production of Antibodies to Human Interferons in Mice", *Infection and Immunity,* 19:570–574 (1978), by Dalton et al.

"Interferons and Their Actions", Editors Stewart and Gottlieb, CRC Press, Boca Raton, Fla., pp. 54–61 (1977).

"Sequential Antibody Affinity Chromatography of Human Leukocyte Interferon", *Scand. J. Immunol.,* 6:77–85 (1977), by Berg.

"Antigenic, Physicochemical, and Biologic Characterization of Human Interferons", *Annals of New York Academy of Sciences,* pp. 703–710 (1976), by Vilcek et al.

"Affinity Chromatography of Human Leukocyte and Diploid Cell Interferons on Sepharose-Bound Antibodies", *The Journal of Immunology,* 114:640–644 (1975), by Berg et al.

"Derivation of Specific Antibody-Producing Tissue Culture and Tumor Lines by Cell Fusion", *European Journal of Immunology,* 6:511–519 (1976), by Kohler and Milstein.

"Continuous Cultures of Fused Cells Secreting Antibody of Predefined Specificity", *Nature,* 256:495–497 (1975), by Kohler and Milstein.

*Primary Examiner*—John Tarcza
*Attorney, Agent, or Firm*—Richards, Medlock & Andrews

[57] ABSTRACT

A hybridoma continuous cell line, capable of producing monoclonal antibodies specific for all species of human interferon-alpha, is disclosed. A method for producing hybridomas and monoclonal antibodies with the required specificity is also disclosed. Methods of use of the disclosed compositions for purifying human interferon-alpha, screening blood in blood banks, and for producing specific polyclonal antibodies are claimed and detailed.

2 Claims, No Drawings

PRODUCTION OF HYBRIDOMA ANTIBODIES FOR INTERFERON

This is a continuation-in-part of Ser. No. 586,019, filed Feb. 3, 1984, now abandoned.

TECHNICAL FIELD

This invention relates to the production, characterization and use of antibodies specific to at least one common antigenic determinant among closely related proteins belonging to the human interferon-alpha (HUIFN-α) system.

BACKGROUND OF THE INVENTION

Interferons are now widely recognized as being an important group of biological proteins capable of rendering cells or whole organisms resistant to virus attack. Furthermore, interferons have been proven to play a significant role in the regulation of the immune system in vivo and in vitro and exhibit numerous other so-called non-viral activities such as antiprotozoal and antibacterial activities, antiproliferative activity of tumor cells, potentiation of the natural killer cell system, and potentiation of the Human Leukocyte Antigen (HLA) System. As such, it is believed interferons are proteins with tremendous potential in the clinical area.

The clinical and therapeutic application of interferon, however, has been slow due to both the high cost of obtaining human interferon and the inability to obtain pure human interferon. Additionally, recent developments in interferon research revealed that several different classes of human interferons exist. Specifically, three different classes of interferon have been demonstrated: leukocyte (HUIFN-α), fibroblast (HUIFN-β) and immune (HUIFN-gamma) interferons. These classes correspond to the cell type employed as the source of human interferon, those being buffy coat leukocytes, fibroblasts and immunocompetent lymphocytes, respectively. Each of these classes in turn have been shown to demonstrate variable activities with respect to the aforementioned viral and non-viral activities attributed to interferon generally. It has, therefore, become desirable to develop the ability to isolate and generate pure interferon of each of the designated classes. Attempts to isolate each of these interferon classes, however, have been further complicated by the discovery that within, for example, the leukocyte interferon class, as many as thirteen species exist.

Whereas classical techniques for protein purification, such as gel filtration, high performance liquid chromatography and antibody affinity chromatography employing polyclonal antibodies specific to interferons, have been employed to isolate and partially characterize the aforementioned classes and intra-class species of human interferon, these techniques cannot be economically employed to isolate sufficient quantities of all pure interferon species for pharmaceutical and/or diagnostic use. There is, therefore, a critical need to develop a means for economically isolating the pure human interferon species.

Employment of the new hybridoma technology for monoclonal antibody production should provide a means for economically isolating large quantities of pure human interferons. The hybridoma technique for producing monoclonal antibodies, as originally described by Kohler and Milstein, comprises fusing spleen lymphocytes with malignant cells (myelomas) derived from a malignant cell line so as to create a fused cell hybrid cell line which possesses charcteristics of both the lymphocytes and myeloma cells (See Kohler and Milstein, Nature 256: 496–497 (1975)). The fused cell hybrids, called hybridomas, produce and secrete a single type of immunoglobulin (antibody) and are immortal. The combination of these two features allows for the continuous and reproducible production of a single tye of antibody molecule by the hybrid cells. The traditional techniques of immunizing an animal with an immunogen (usually consisting of the desired antigen together with impurities, each antigen having a variable number of epitopes) and thereafter collecting the sera from the immunized animal yield a mixture of many different antibodies having different specificities (the ability to recognize or bind with certain epitopes). Antibodies to antigenic impurities in the immunogenic preparation may also be developed by the immunized animal. Moreover, this mixture of antibodies can almost never be reproduced identically.

In both the traditional and hybridoma methods for producing antibodies, the specificity of the antibodies produced thereby depends upon the antigen or antigens presented (used to immunize) to the animal. Therefore, the traditional technique often produces a mixture of desired and undesired antibodies and it may be difficult to separate out the undesired portion. The hybridoma technique makes it possible to produce pure antibody preparation.

Recently, various monoclonal antibody preparations have been produced which have been claimed to be specific to various species of human interferon-alpha (HUIFN-α). As is discussed below, however, none of these antibody preparations contain antibodies capable of simultaneously recognizing all thirteen known species of human interferon-alpha.

U.S. Pat. No. 4,423,147 to Secher et al. and the publication by Secher and Burke, Nature 285: 446 (1980), discloses the preparation of a monoclonal antibody specific to one species of HUIFN-α, that being a species having a molecular weight of about 18,000. The monoclonal antibody generated in the '147 patent was produced by first immunizing mice with a crude preparation of lymphoblastoid interferon and thereafter fusing antigen primed mouse spleen lymphocytes with myeloma cells to create a hybridoma cell line.

The publications by Staehelin et al., Proceedings of the National Academy of Sciences 78: 1848, Imai et al., Journal of Immunology 128: 2824–2825, and Novick et al., Journal of Immunology 129: 2244 (1982), disclose the preparation of hybridoma cell lines, each of which produce a monoclonal antibody to but a single species of recombinant interferons or only a few species, of native HUIFN-a.

In order to provide for the economical clinical application of HUIFN-α comprising all species of HUIFN-α, it became, therefore, desirable to develop monoclonal antibodies which will recognize all native species of the HUIFN-α class and develop a process by which such antibodies could be produced. A monoclonal antibody has now, surprisingly, been made having the non-expected property of capability of binding all twelve native species of HUIFN-α. This increased recognition capability represents a significant improvement to the art.

SUMMARY OF THE INVENTION

The present invention relates to a method for producing a continuous cell line capable of producing antibodies against at least one common antigenic determinant among closely related proteins (species) belonging to the HUIFN-α system. A continuous cell line capable of continuously producing said antibodies is disclosed, and one example thereof has been deposited with the American Type Culture Collection (ATCC), Rockville, Md. 20852-1776, and assigned designation number HB 8619.

In another aspect of the present invention, compositions comprising monoclonal antibodies capable of reacting specifically against a common antigenic determinant among closely related proteins of the HUIFN-α system are disclosed.

In yet another aspect of the represent invention, methods for using the compositions disclosed are set forth.

DETAILED DESCRIPTION OF THE INVENTION

The present invention concerns the manufacture of a hybridoma cell continuous cell line, comprising a fusion between an antibody-producing cell from an immunocompetent animal and, generally, a myeloma cell. A myeloma cell is a preferred component because of its ability to reproduce an indefinite number of times and to impart this characteristic to the hybridoma. However, any equivalent for said myeloma cell in function may be used. The description "immortal cell" is intended to encompass myeloma cells and those with equivalent functions. Such a hybridoma is said to be "capable of producing monoclonal antibodies" because genetic material responsible for coding for antibody production and secretion is incorporated into the hybridoma from the antibody-producing cell so that a single kind of antibody is produced by the hybridoma. The antibody-producing cell is isolated from an animal which has been induced to produce particular antibodies by repeatedly introducing particular antigenic determinants to the animal's immune system. The immunization schedule and dosages may vary. One effective schedule is fully described in Example I (B); however, it should be noted that other schedules and dosages may produce effective results.

The immunogen is preferably treated with sodium dodecyl sulfate in an amount effective to denature a crude or semipurified preparation of human interferon-alpha. A preferred range is from 0.01% to about 5% by volume of immunogen. It has been previously reported that at least 13 species of human interferon-alpha exist, each having a distinct molecular weight and also interferon activity, that is, the ability to protect cells from viral attack. It has now been found that all known human interferon-alpha species, comprising more than 98 % of the total biological activity of the HUIFN-α (Leukocyte) origin, have at least one common antigenic determinant which may be recognized by antibodies of the present invention. An antibody is said to be "specific for" a particular antigenic determinant if it recognizes that determinant and binds to a site on or near that determinant because of that recognition.

In accordance with the present invention, a new hybridoma has been developed and named LO-22. This hybridoma has been deposited with the American Type Culture Collection in Rockville, Md., and is designated ATCC HB 8619.

The monoclonal antibodies produced by hybridomas made according to the present invention are useful in many ways. Some uses are: purifying human interferon proteins in a one-step procedure, and testing for interferon in human patients. The advantage of the antibodies produced in accordance with the present invention is their ability to recognize all known native species of human interferon-alpha. Hybridoma cells may be "caused to produce" monoclonal antibodies by providing appropriate media to said hybridomas.

It is contemplated that industries and laboratories will find these new monoclonals useful for obtaining large quantities of pure human interferon proteins. A monoclonal antibody specific for a given antigen will draw that antigen out of a mixture of antigens when that antibody is contacted with a mixture containing the given antigen. Means for separating antibody-antigen complexes from non-bound material may then be employed. For example, the monoclonal may be affixed to an insoluble, inert solid. If the given antigen is present in a liquid allowed to contact the immobilized monoclonal, it will be brought into the "solid phase." Methods for separating solid from liquid may then be used. The interferon protein antigens may then be separated from the monoclonal antibody by methods known in the art to cause the bond to be broken, such as changing the pH or other means. An affinity column which links the monoclonal antibody to an inert filler is one example of such a process. In addition, the monoclonals may be used by blood banks to screen blood for interferon. Because blood may contain elevated levels of interferon only if viral infection has been present, the blood may be quickly screened for multiple possible viral contaminants without the necessity for individual antibodies specific for each possible virus. Blood containing high interferon levels may be labeled high risk and discarded from the transfusion pool. The high risk blood may optionally be further tested for specific contaminants. For example, Acquired Immune Deficiency Syndrome (AIDS) patients will often have a particular acid-labile species of human interferon-α in their blood, as well as an elevated level of interferon generally, for which the antibodies of the instant invention bind to. This acid labile species may be tested for in a further test in which the effect of acid on interferon activity is noted.

The following examples are intended to provide specific methods for making the hybridomas and monoclonal antibodies of the instant invention and use thereof. It should be understood that minor variations such as may be possible by genetically engineering the claimed invention are within the scope of this invention. In addition, it is recognized that the disclosure of this new monoclonal antibody will allow isolation of the antigen to which it binds which is common to all human interferon-α species. This antigen may be used as an immunogen to cause animals to produce polyclonal antibodies with great specificity toward human interferon-alpha. Such polyclonals are intended to be within the scope of this invention.

Finally it should be recognized that all subcultures of ATCC HB 8619 are encompassed by this invention. A subculture is any culture made from the deposited culture.

EXAMPLE I

Preparation of Hybridoma Cells

A. Preparation of the Immunogen

Crude Human leukocyte interferon-α was concentrated according to the method of Berg and Heron, *Scandanavian Journal of Immunology* 11: 289–502 (1980), which is herein incorporated by reference. The crude interferon was partially purified according to the following technique: Fifteen-million units of human leukocyte interferon in the form of crude concentrated interferon (CIF) (dialyzed against phosphate buffered saline (PBS) pH 7.4) was diluted two-fold with loading buffer comprising 0.1 molar sodium acetate and 0.3 molar sodium chloride pH 7.2. The interferon solution was loaded onto a 5 ml highly absorbed polyclonal rabbit antibody column. The antibodies employed on the column were thought to be directed mainly against the human leukocyte interferon proteins as described previously by Berg et al. in *Scandanavian Journal of Immunology* 8: 429–436 (1978), incorporated herein by reference. Fractions were collected and after a thorough wash which bought the absorbance of 280 nanometers back close to the original base line, the column was eluted by applying 0.1 molar acetic acid and 0.3 molar sodium chloride, pH 2.4 (a small amount of citric acid was included in the buffer to achieve proper pH). The interferon activity was collected in the fractions in which a pH drop was noted. The fractions were all pooled and the final volume equaled 10 milliliters. Approximately 70% of the interferon activity was recovered in these 10 milliliters, and the specific activity of the purified interferon was $10^7$ International Interferon Units (hereinafter IFN units) per milligram protein. 100 microliters of a 10% solution of sodium dodecyl sulfate (SDS) (obtained from Sigma Chemical Company, St. Louis, Mo.) was added to the purified interferon solution and mixed well. Aliquots were made containing 100,000 units interferon each. Aliquots were kept frozen at $-20°$ C. until use, interferon activity maintaining stability for at least six months. These preparations were used as the immunogen.

B. Immunization of Mice

Four to six-week-old, female BALB/C mice were initially injected (i.p.) with 100,000 IFN units of human interferon (isolated in Part A) mixed with an equal volume of Freund's Adjuvant (obtained from Gibco, Grand Island, N.Y. 14072). Each dose was in a total volume of 150–200 microliters. Each mouse was given 5–8 total injections, one per week, of about 30,000 IFN units of human interferon without adjuvant. Follow-up injections, one per week, consisted of 30,000 units of human interferon without Freund's Adjuvant. Mice were tested for production of antibodies to human interferon by taking individual blood samples from the tail of each mouse, and testing each sample for production of antibodies via the "traditional" neutralization test. When antibodies were present, the mice were injected with 100,000 interferon units (half i.p. and half subcutaneously) without Freund's Adjuvant, 2 to 5 days before the mice were to be sacrificed and their serum, containing antibodies obtained. The "traditional" neutralization test was performed according to the method of Berg, *Scandanavian Journal of Immunology* 6: 77–86 (1977), herein incorporated by reference.

C. Fusions of Antibody-Producing Cells with Myeloma Cells

The mice immunized in Part B were sacrificed and their spleens removed in an aseptic manner. The spleen was cut asceptically and transferred to a glass tube containing 2–4 ml of 10% Roswell Park Memorial Instituted Media (RPMI) 1640 and homogenized at 2° C. by means of a glass piston. The suspension was filtered through a cotton filter and washed twice. A mouse myeloma cell line (P3×63 NS1, HPRT-deficient, produces Kappa, non-immunoglobulin secreting; obtained from the Human Genetic Mutant Cell Repository, Copewood and Davies Street, Camden, N.J. 08103, Cat. #GM 3573) was grown in RPMI 1640. (purchased from Gibco) along with 10% new born calf serum (also obtained from Gibco), with 1% penicilin, 1% streptomycin, and 1% gentamycin as described by Lovborg, *Monoclonal Antibodies: Production and Maintenance*, London pp. 1–65 (1982), herein incorporated by reference. A mycoplasma test was completed on the myeloma cells.

If the mycoplasma test proved negative, a fusion procedure was initiated. The procedure of Lovborg, *Production and Maintenance*, London, pp. 1–65 (1982), herein incorporated by reference, was utilized. The presence or absence of living fused splenocyte and myeloma cells (hydridomas) was determined by microscopic inspection at $2\times$ to $10\times$ power and subsequently verified by several inspections in order to follow the growth of any cells which appeared to expand into clones in 8–25 days.

Supernatants from individual wells in the incubation plate containing living clones were tested for anti-interferon antibodies by the procedure described in Example II.

EXAMPLE II

Selection of Anti-Interferon Producing Hybridomas by a Semi-Solid Binding Assay

A. Binding Anti-Mouse Antibody to Wells

A 96-well plate was obtained from Nunc, Denmark. A 300 microgram/ml solution of rabbit anti-mouse immunoglobulin (DAKO-PATT, Denmark) in phosphate buffered saline (PBS), pH 7.2 (Gibco) including 0.05% sodium azide was added to each well of the plate. The plate was incubated at 37° C. for one hour, then at 4° C. for 24 hours. Washing Buffer (phosphate buffered saline with 0.05% sodium azide and 0.05% Tween 80 (obtained from Sigma Chemical Co., St. Louis, Mo.)) was used to wash each well three times. A 2% solution of egg albumin (Sigma Chemical Co., St. Louis, Mo.) in phosphate buffered saline was then added to each well. The plate was then incubated for two hours at 25° C. The wells were then washed three times with Washing Buffer.

B. Reacting Mouse Anti-Interferon Antibody with Plate-Bound Anti-Mouse Antibody Supernatant from hybridoma cultures was then tested for anti-interferon antibody by adding 100 microliters of said supernatant to each well prepared in Part A. Each well was made to contain 0.05% sodium azide. The plate was incubated at 25° C. for 24 hours. The wells were then washed twice with Washing Buffer, then twice with Washing Buffer without sodium azide. The wells now contained bound anti-mouse antibody/mouse antibody complexes.

C Reacting Human Interferon with Plate-Bound Anti-Mouse Antibody/Mouse Anti-Human Interferon Complexes A native HUIFN-α (leukocyte) solution, containing 0.1 to 0.3 IFN units in total, was prepared by diluting a standard preparation containing 7,000 units per ml, 20,000 and 70,000 times respectively in RPMI 1640 medium including 5-10% cow serum. 100 microliters of the solution equivalent to 0.1 IFN unit was added to the wells prepared in Part B, and incubated for two hours at 25° C. The method described in the following reference was utilized: W. Stewart, II. The *Interferon System*, Springer-Verlag at 17-18 (1979), herein incorporated by reference. The supernatant of the wells was then assayed for residual interferon. A residual amount of interferon implied the absence of detectable hybridoma antibody having the desired binding specificity.

D. Assay for Residual Interferon

MDBK cells (American Type Culture Collection, Rockville, Md.) were grown to confluency in wells fo 96 well-microtrays, (obtained from Nunc, Denmark). 100 microliters of supernatant from one of the reaction wells of Part C was added to MDBK microwell, which had been drained in advance. The microtrays were incubated at 37° C. for 20 hours (5% $CO_2$). VSV, a virus obtained from American Type Culture Collection, was then added to the microwells in a concentration sufficient to yield a distinct cytopathogenic effect subsequent to 12-16 hours incubation. The proper VSV concentration used above was determined by performing biotitrations as follows: 10-fold dilutions performed in RPMI 1640, including 1-2% calf serum, were accomplished using virus stock ampules kept at −70° C. The individual dilutions were added to the respective wells in triplicate and incubated overnight at 37° C. in 5% $CO_2$. The highest dilution yielding a distinct cytopathogenic effect was chosen as the standard dilution used in the above interferon titrations. This so-called dilution was estimated in advance before the actual titration took place.

EXAMPLE III

Propagation of Anti-Interferon-Producing Hybridomas

Hybridomas identified as positive for anti-interferon antibody production were allowed to grow until half the bottom of the well was covered by cells. A suspension was made by mixing the medium with the cells and half the suspension was injected into Pristane-primed mice (i.p.). The other half was cloned by means of the so-called limited diluting cloning technique described in Lovbourg *Production and Maintenance*, Trowbridge, London (1982), herein incorporated by reference, using 96-well flat bottom microtrays (Nunc, Denmark) to which macrophages had been seeded 24 hours in advance. The macrophages harvested from one mouse were suspended in 20 ml RPMI 1640 containing 5% calf serum. Two full dilutions were made from half the saved hybridoma cell suspension. 100 ml of this suspension was distributed evenly in triplicate into the macrophage-covered 96-well panels. The panels were wrapped with plastic wrap and incubated at 37° C. and 5% $CO_2$ for several days. At a certain dilution only one clone was seen. These single clones were then allowed to grow to confluency. Once confluent, all the cells were transferred into a small 10 ml plastic bottle using 2 ml of RPMI 1640 with 10% calf serum protein. After three to five days, half of the cells were injected into Pristane primed mice (i.p) (1 to $10 \times 10^4$ Cells). After five to twelve days, scites fluid was harvested from the mice. The ascites fluid contained more hybridoma cells, which had been propagated from the injected cells, and anti-interferon antibody which had been produced by the hybridoma cells and exuded into the ascitic fluids.

EXAMPLE IV

Isolation of Anti-Interferon Antibodies

Ascites fluid obtained according to the procedure set out in Example III was cooled to 4° C. to prevent enzymatic degradation of antibodies. Immediately thereafter, hybridoma cells and other debris were removed by centrifuging at $2000 \times g$ for 20 minutes at 4° C. The supernatant was saved. Immunoglobulins were precipitated by the ammonium sulfate method. This procedure was done as follows: An equal volume of saturated ammonium sulfate (ammonium sulfate was bought from Merck Chemical, West Germany) was mixed with the ascites fluid by slowly adding, drop-wise, the saturated ammonium sulfate to the ascites fluid over a period of half an hour. Mixing was performed by means of a magnetic stirrer. The precipitate was centrifuged at $10,000 \times g$ for half an hour at $+4°$ C. and the ammonium sulfate precipitate was kept at $-20°$ C. for storage, etc. The antibodies were tested for anti-interferon specificity according to the method of Example II, substituting antibody solution herein obtained for the supernatant from hybridoma cultures used in Example II, Section B.

EXAMPLE V

Characterization of Anti-Interferon Antibody Capable of Recognizing at Least 12 Species of HUIFN-α

Affinity chromatography was carried out on crude, native leukocyte interferon by coupling the isolated anti-interferon antibodies obtained in Example IV to cyanogen bromide-activated sepharose as described in Berg, *Scandanavian Journal of Immunology* 6: 78–86 (1977), herein incorporated by reference. The equilibrated column was loaded with 90 mls of the crude interferon. The column was washed with Washing Buffer (0.1M sodium acetate, 0.3M NaCl, pH 7.2). The wash (WASH I) was saved and set aside. Elution was accomplished by running eluting buffer (1M acetic acid 0.3M NaCl and citric acid to achieve pH 2.4) through the column. The eluate (ELUATE I) contained 96% of the interferon put on the column, indicating it had bound to the antibodies on the column.

WASH I (30–40 mls) was concentrated to 4 mls by means of sucrose dialysis. The 30–40 ml was transferred to a dialysis tubing and surrounded by crystalline sucrose. This was wrapped into aluminum foil and kept at 4° C. overnight whereby a 10-fold concentration had occured. The concentrated wash was loaded on the same CNBr-antibody column. The column was washed with Washing Buffer and the wash saved (WASH II). The column was eluted with eluting buffer and the eluate saved (Eluate II). The WASH II was analyzed by the traditional neutralization test by adding 100 microliter of anti-human interferon-β diluted 1 to 1000 which was produced by immunizing a rabbit with 5 million units of partially purified fibroblast interferon, to 100 microliters of WASH II. ELUATE I was not able to neutralize anti-human interferon-β under the same conditions. WASH II contained 50.0 units of human interferon-β (HUIFN-β).

ELUATE I was analyzed on analytical thin-slab sodium dodecyl sulfate polyacrylamide gel electrophoresis (SDS-PAGE) by the procedure in Berg and Heron, *Scandanavian Journal of Immunology* 6: 78–86 (1977), herein incorporated by reference. 100 ul of ELUATE I was mixed with 25 ul of electrophoresis buffer + glycerol and loaded to the 5% stacking gel. Molecular markers (14,400, 20,600, 30,000) were loaded to several slots. The height of the stacking gel was 7 cm, the hieght of the gradient gel (12–22%) was approximately 25 cm and the thickness was 0.75 mm. After overnight electrophoresis, the gel was stained and the partially destained gel was rapidly transferred to a transparent plastic sheet whereby the precise location of the protein bands was made possible subsequent to cutting the individual bands. The individual gel slices were smashed and the protein content was eluated into 1 ml medium containing 5% serum (at room temperature for five hours) and left a 4° C. overnight subsequent to interferon titration. No interferon activity was found in the fraction below 15,000. The pattern of HUIFN-α species was then examined.

All 12 species of HUIFN-α were found to be located in the molecular weight range of 16,000–25,000. Probably, the column is also able to recognize not previously detected species of HUIFN-α with a higher molecular weight since fractions containing interferon activity were also found around 30,000.

The immunoglobulins able to recognize all 12 species of HUIFN-α were produced from the hybridoma manufactured according to Examples I–III named "LO-22." LO-22 hybridoma cells have been deposited with the American Type Culture Collection, Rockville, Md., ATCC #HB 8619.

The immunoglobulins produced from the LO-22 hybridoma cells were characterized as belonging to the IgG-class by means of Ouchterlony-tests in whch several fractions of the ascites fluid (and supernatants from cultured LO-22 cells) were checked against rabbit anti-mouse immunoglobulins (DAKO-PATT, Denmark; Behring Werke, W. Germany) or goat antimouse IgG F(ab)2 (Cappel) or goat anti-IgM (heavy chain) (Cappel). A heavy precipitate was seen especially between the hybridoma antibodies, LO-22, and goat anti-mouse IgG F(ab)2 antiserum (Cappel).

EXAMPLE VI

Use of LO-22 Antibodies for Detection of Low Levels of Human Interferon-Alpha

A stock solution containing two milligrams per ml of purified LO-22 monoclonal antibody was prepared, and a 1 to 250 dilution was made in buffer a containing 0.05 molar sodium azide. 100 microliters of the 1:250 dilution of LO-22 was added to each well of a 96-well microtitration plate, and the panel was then covered with a plastic film and allowed to incubate at 37° C. for three hours, then transferred to 4° C. 100 microliters of phosphate buffered saline (PBS) containing 2% inactivated human serum and 1% inactivated calf serum was added to each well and incubated for 30 minutes at room temperature. Each well was then washed four times with Reagent D (citrate/phosphate buffer 0.1M pH=5.0 made by adding 7.30 grams citric acid, H2O to 23.87 grams Na2HPO4, 12 H2O, bringing to one liter). The last wash was allowed to stand for one minute. 100 microliters of 2% human serum and 1% calf serum was added to all the wells. The sample suspected to contain interferon was added to each well in a volume or 50 to 100 microliters. The panel was sealed by means of a plastic film and placed on an appropriate mixer and allowed to mix for at least two minutes at room temperature. The panel was then incubated overnight at +4° C. in the dark. The panel was kept in a horizontal position throughout all the operations. After incubation each well was washed four times with Reagent B (phosphate buffered saline pH=7.4, 0.05% Tween 20). The last wash was allowed to stand for one minute. A stock ampule of biotinylated steer anti-human interferon-a antibody conjugate, (the steer polyclonal antibody component obtained by immunizing animals with human interferon-a, collecting serum, and precipitating out the antibodies by conventional methods) in 50% Esolineglycol was diluted by adding 5 microliters to 10.5 milliliters PBS containing 2% human serum and 1% calf serum. The dilution was incubated at 15 minutes at room temperature in the dark before usage. 100 microliters of the diluted solution was then added to each well and incubated for 30 minutes at 37° C. The wells were then washed with Reagent B three times. The panel was emptied by decantation. 100 microliters of streptavidin-peroxidase (obtained from Bethesda Research Laboratories, U.S.) was diluted 1:1200 in 1% bovine serum albumin in phosphate buffered saline and incubated for one hour at room temperature. Each well was then washed five times with Reagent B. The last wash being allowed to stand for at least two minutes. The panel was emptied by shaking up and down gently. 100 microliters orthophenylindiamine 10 mg/ml in Reagent D, including 35% $H_2O_2$, was added to each well and allowed to incubate at room temperature for 15–30 minutes in the dark. The reaction was stopped by adding 50 microliters of 1M $H_2SO_4$ to each well. The results were read spectrophotometrically at 492 nm. Comparison was made to a standard curve in which known concentrations of interferon were present. It was found that the assay was effective to detect interferon in the range of about 1 to about 260 IFN units.

EXAMPLE VII

Use of LO-22 Antibodies for Detection of Human Interferon-Alpha

A stock solution containing LO-22 monoclonal antibodies 2 mg/ml was prepared. This was diluted by adding 40 microliters to 10.5 milliliters PBS, pH 7.4 yielding a 1:250 dilution. The diluent PBS was prepared by adding 1.5 grams of $K_2HPO_4$, $3H_2O$ to 0.34 grams $KH_2PO_4$ and 8.00 grams NaCl and bringing the mixture to one liter with $H_2O$. The PBS was made 0.05 molar in sodium azide. 100 microliters of the 1:250 dilution was added to each well and the panel covered with a plastic film and left at 37° C. for at least three hours, then transferred to 4° C. The panel was kept horizontal. It was found that the plate can be prepared as early as two to three weeks before the interferon assay is to be performed provided it was kept at 4° C. in the dark. 100 microliters of PBS containing 2% inactivated human serum and 1% inactivated calf serum was added to each well and allowed to incubate for 30 minutes at room temperature. The plates were then washed four times with Reagent B (PBS pH 7.4, 0.05% Tween 20). The last wash was allowed to stand for one minute. 100 microliters of the sample suspected to contain interferon in an appropriate dilution was added. An appropriate dilution would be a dilution yielding interferon concentration in the range of 100 to 5000 IFN units per ml. The mixture was incubated at one hour at room temperature. The interferon dilutions were performed in PBS with 2% human serum plus 1% calf serum. After incubation the plate was washed four times with Reagent B, the last wash being allowed to stand for one minute. 100 microliters of steer anti-human leukocyte interferon peroxidase conjugate (the steer antibodies obtained by injecting the animals with human interferon, collecting serum, and precipitating out the antibodies by conventional methods) diluted 1:400 in PBS containing 2% human serum and 1% calf serum was added to the wells and incubated at room temperature for one hour. The mixture was washed five times, the last two washes being allowed to stand for least one minute each. 200 microliters of Reagent D (citric acid 7.3 grams $Na_2HPO_4$, 12 $H_2O$ 23.87 grams to one liter (0.1 molar citrate phosphate buffer pH 5.0)) was added to the wells and incubated for at least three minutes to ensure detergent removal. The wells were emptied each time by shaking them upside down and tapping gently on the back side until almost dry panels are obtained. Ortho-phenylenediamine, 10 miligram per 10 ml in Reagent D including 10 microliters 35% $H_2O_2$, was added to each well in the amount of 100 microliters. This was incubated at room temperature for 15 to 30 minutes in the dark. The reaction was stopped by adding 50 microliters of one molar $H_2SO_4$ to each well. The reaction was read spectrophotometrically at 492 nanometers. A standard curve of known concentrations of interferon was performed and the absorbance of the unknown sample compared to the standards. The concentration of interferon in the unknown sample was calculated by extrapolating to the standard curve. It was found that interferon in the range of 30 to 5000 IFN units could be detected by this method.

EXAMPLE VIII

Use of LO-22 Antibodies to Detect Acid-Labile Human Interferon-Alpha in the Blood of Persons with Acquired Immune Deficiency Syndrome (AIDS)

A blood sample is taken from person suspected to have acquired immune deficiency syndrome (AIDS). The serum is obtained by centrifuging the whole blood at 2000×g for several minutes. LO-22 antibodies are bound to a plate as described in Example VI and Example VII. Interferon detection is accomplished by use of the assay described in either Example I or Example II. If interferon is detected, further characterization of the type of interferon is performed by the following method: determining if interferon activity is destroyed, addition of dilute (1N) in hydrochloric acid to the titration scheme to effect a pH drop to 2.5 for at least 4 hours, preferably overnight at 4° C. The pH was then brought to 7.2 by means of dilute NaOH (1N). Interferon can be titrated by method known in the art.

Presence of the acid-labile interferon (as determined by loss of interferon activity) indicates the possibility of AIDS.

EXAMPLE IX

Use of LO-22 Antibodies to Screen for Virus Contaminated Blood in Blood Banks

LO-22 antibodies are to be bound to plates as described in Example VI or Example VII. Serum from donated blood is obtained and tested for the presence of interferon according to one of the assays set forth in Example VI or VII. Presence of a high amount of interferon in the blood sample indicates that the donated blood from the particular individual should not be used for transfusion purposes. The blood bank may routinely perform tests for high levels of interferon, a high level indicating persence of viral infection in the donor. The blood deemed unsuitable for transfusion purposes may be tagged by the blood bank and that blood may be optionally made subject to further diagnostic procedures for the benefit of the donor. However, in the initial screening procedure, the blood bank is successful in eliminating high risk blood from the transfusion pool without the disadvantage of performing different tests for every suspected viral contaminant present.

I claim:

1. A process for a producing a hybridoma cell capable of producing monoclonal antibodies specific for least one antigenic determinant common to all species of Human Interferon-alpha, comprising the steps of:
    (a) immunizing an animal with an immunogen comprising Human Interferon-alpha proteins admixed with an effective amount of sodium dodecyl sulfate to denature said proteins; and
    (b) thereafter removing at least one antibody-producing cell from said animal and fusing genetic material from said antibody-producing cell with an immortal cell to form said hybridoma cell.

2. A process according to claim 1 wherein said effective amount of sodium dodecyl sulfate is between about 0.01% to about 5% by volume of immunogen.

* * * * *

UNITED STATES PATENT AND TRADEMARK OFFICE
CERTIFICATE OF CORRECTION

PATENT NO. : 4,902,618
DATED : February 20, 1990
INVENTOR(S) : Kurt F. Berg

It is certified that error appears in the above-identified patent and that said Letters Patent is hereby corrected as shown below:

```
Column 2, line 4, "497" should be --597.
Column 2, line 9, "tye" should be --type--.
Column 3, line 17, "represent" should be --present--.
Column 5, line 8, "289" should be --489--.
Column 8, line 4, "Cells" should be --cells--.
Column 8, line 5, "scites" should be --ascites--.
Column 9, line 34, after "I-III" insert --and--.
Claim 1, line 1, after "for" delete "a".
Claim 1, line 2, after "for" add --at--.
```

Signed and Sealed this

Third Day of December, 1991

Attest:

HARRY F. MANBECK, JR.

*Attesting Officer*       *Commissioner of Patents and Trademarks*